US010499874B2

United States Patent
Nagai

(10) Patent No.: US 10,499,874 B2
(45) Date of Patent: Dec. 10, 2019

(54) MANAGEMENT SYSTEM FOR X-RAY DETECTOR AND X-RAY DIAGNOSIS APPARATUS

(71) Applicant: Toshiba Medical Systems Corporation, Otawara-shi (JP)

(72) Inventor: Seiichirou Nagai, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 789 days.

(21) Appl. No.: 14/530,021

(22) Filed: Oct. 31, 2014

(65) Prior Publication Data
US 2015/0146850 A1    May 28, 2015

(30) Foreign Application Priority Data
Nov. 22, 2013   (JP) .................... 2013-241656

(51) Int. Cl.
*A61B 6/00*          (2006.01)
*G01D 1/18*          (2006.01)
(Continued)

(52) U.S. Cl.
CPC ............ *A61B 6/542* (2013.01); *A61B 6/5294* (2013.01); *G01D 1/18* (2013.01); *H05G 1/28* (2013.01);
(Continued)

(58) Field of Classification Search
CPC ......... A61B 5/7221; A61B 6/465; A61B 6/52; A61B 6/5294; A61B 6/54; A61B 6/542;
(Continued)

(56) References Cited

U.S. PATENT DOCUMENTS

2006/0215807 A1   9/2006 Ohara
2006/0239415 A1   10/2006 Liu et al.
(Continued)

FOREIGN PATENT DOCUMENTS

JP      2004-097634 A       4/2004
JP      2006-297096         11/2006
(Continued)

OTHER PUBLICATIONS

Japanese Office Action dated Nov. 7, 2017, issuing in corresponding Japanese Patent Application No. 2013-241656, citing documents AO-AR therein (5 pages).

*Primary Examiner* — Anastasia Midkiff
(74) *Attorney, Agent, or Firm* — Oblon, McClelland, Maier & Neustadt, L.L.P.

(57) ABSTRACT

The management system of the X-ray detectors according to the embodiments detects X-rays irradiated from the X-ray generator when X-ray imaging is carried out, and includes an inspection unit and a validity period setting unit. The inspection unit inspects at least one of performance, function, and operation of an actual operation state of the X-ray detector. The validity period setting unit sets a validity period which is a criterion for determining whether the inspection results inspected are valid or not. The system is configured that the X-ray imaging is not performed on a subject when the inspection results are determined to be invalid based on the validity period.

9 Claims, 7 Drawing Sheets

(51) Int. Cl.
  *H05G 1/28* (2006.01)
  *G06T 1/00* (2006.01)
  *A61N 5/10* (2006.01)
  *H05G 1/30* (2006.01)

(52) U.S. Cl.
  CPC .............. *A61B 6/467* (2013.01); *A61B 6/566* (2013.01); *A61B 6/581* (2013.01); *A61B 6/582* (2013.01); *A61B 2560/0266* (2013.01); *A61N 5/1064* (2013.01); *G01N 2223/302* (2013.01); *G01N 2223/303* (2013.01); *G06T 1/0014* (2013.01); *H05G 1/30* (2013.01)

(58) Field of Classification Search
  CPC ........... A61B 6/545; A61B 6/58; A61B 6/582; A61B 6/585; A61B 6/586; A61B 2560/00; A61B 2560/02; A61B 2560/0223; A61B 2560/0266; A61B 2562/00; H05G 1/00; H05G 1/08; H05G 1/26; H05G 1/30; H05G 1/54; H05G 1/56; H05G 1/60; H05G 1/28; A61N 5/00; A61N 5/10; A61N 5/1048; A61N 5/1064; A61N 5/1075; A61N 2005/0626; G01T 1/00; G01T 1/1648; G01T 1/17; G01T 1/175; G01T 7/00; G01T 7/005; G01D 1/18; G01D 18/00; G01D 18/002; G01D 18/006; G01N 2223/00; G01N 2223/30; G01N 2223/302; G01N 2223/303; G01N 2223/304; G01N 2223/306; G06T 1/00; G06T 1/0007; G06T 1/0014; H01L 27/144; H01L 27/146; H01L 27/14601; H01L 27/14658; H01L 27/148; H01L 27/14806
  See application file for complete search history.

(56) References Cited

U.S. PATENT DOCUMENTS

| | | | |
|---|---|---|---|
| 2010/0054399 | A1 | 3/2010 | Nishino et al. |
| 2011/0013220 | A1* | 1/2011 | Sabol .................... G06Q 50/22 358/1.15 |
| 2011/0235782 | A1 | 9/2011 | Kamiya et al. |
| 2011/0274244 | A1 | 11/2011 | Jabri et al. |
| 2014/0010353 | A1* | 1/2014 | Lalena .................. A61B 6/465 378/98 |

FOREIGN PATENT DOCUMENTS

| | | |
|---|---|---|
| JP | 2008-099808 A | 5/2008 |
| JP | 2008-145101 | 6/2008 |
| JP | 2010-75678 | 4/2010 |
| JP | 2011-19905 | 2/2011 |
| JP | 2011-067334 A | 4/2011 |
| JP | 2011-200335 | 10/2011 |
| JP | 2011-203595 | 10/2011 |
| JP | 2011-235091 | 11/2011 |
| JP | 2012-045242 A | 3/2012 |

* cited by examiner

FIG. 6

|  | FIRST DAY | SECOND DAY | THIRD DAY |
|---|---|---|---|
| MORNING | SYSTEM IS ACTIVATED | SYSTEM IS ACTIVATED | SYSTEM IS ACTIVATED |
|  | START-OPERATION INSPECTION |  |  |
|  | EXAMINING PATIENT | START-OPERATION INSPECTION |  |
|  | . | EXAMINING PATIENT |  |
|  | . | . |  |
|  | . | . |  |
|  | . | . |  |
|  | . | . |  |
|  | EXAMINING PATIENT | EXAMINING PATIENT |  |
| EVENING | SYSTEM TERMINATION | SYSTEM TERMINATION | SYSTEM TERMINATION |

MANAGEMENT SYSTEM FOR X-RAY DETECTOR AND X-RAY DIAGNOSIS APPARATUS

CROSS-REFERENCE TO RELATED APPLICATION

This application is based upon and claims the benefit of priority from Japanese Patent Application No. 2013-241656, filed Nov. 22, 2013; the entire contents of which are incorporated herein by reference.

FIELD

The embodiments are related to management systems for X-ray detectors and X-ray diagnosis apparatuses.

BACKGROUND

In the conventional management systems for X-ray detectors, for example, the X-ray detector in mobile X-ray systems is used by being transferred to a different position. The X-ray detector thereby receives environmental stimuli. The X-ray detector is activated according to the environmental stimuli (For example, Japanese Unexamined Patent Application Publication No. 2006-297096).

Further, for example, the system detects one or a plurality of X-ray detectors within operative ranges of imaging sub systems. The system can then determine the state (for example, charging conditions, present linkage) and/or the ability (for example, stored protocol, compatibility) for each of the X-ray detectors (for example, Japanese Unexamined Patent Application Publication No. 2011-235091).

Furthermore, for example, the system includes a plurality of X-ray detectors and a server capable of performing communication therewith, and uses the server to obtain functional conditions, maintenance history, and calibration conditions of the X-ray detectors (for example, Japanese Unexamined Patent Application Publication No. 2011-19905).

Large medical institutions have a plurality of inspection rooms. Modality, such as an X-ray diagnosis apparatus, and the like, is provided in the inspection room. The X-ray diagnosis apparatus includes an X-ray generator which generates X-rays and an X-ray detector which is arranged at the position facing the X-ray generator and detects the X-rays. The X-ray detector is configured to wirelessly transmit/receive signals to/from an image processor of the X-ray diagnosis apparatus, such that the X-ray detector is called a wireless flat-panel detector for mobile X-ray imaging. It is assumed that the wireless flat-panel detector for mobile X-ray imaging is shared between a plurality of X-ray diagnosis apparatuses or between the plurality of inspection rooms.

The X-ray detector released from the position facing the X-ray generator is stored in the inspection room. The X-ray detector is housed in a dock (described later). The X-ray detector is configured that the battery conditions thereof can be obtained during storage (for example, Japanese Unexamined Patent Application Publication No. 2011-203595). Here, the "storage" includes a time when the detector is housed in the dock, and means a period, starting from a time when X-ray imaging for diagnosis, in which X-ray imaging is performed on a subject (patient), is terminated until the next X-ray imaging for diagnosis is started, or a period, starting from a time when the X-ray detector is brought in the medical institution until the first X-ray imaging for diagnosis is started.

The environmental stimuli, state/ability thereof, functional conditions, maintenance history, calibration conditions, battery conditions, and other items for the X-ray detector may be called "items related to the performance and/or function of the X-ray detector", or simply called "first items" or "routine inspection items".

The first items are inspected during the storage of the X-ray detector. The inspection results are stored in a storage inside the X-ray detector or a storage provided in the X-ray diagnosis apparatus. The inspection results are read from the storage and checked by a radiation technician, and the like.

In the inspection items for the X-ray detector, there are items related to operation in actual operation conditions for the X-ray detector. Theses items may simply be called "second items" or "operation-start inspection items". The inspection on the second items is performed just before the X-ray imaging for diagnosis in which the X-ray imaging is performed on the subject.

In the techniques disclosed in the patent gazettes mentioned above, when the X-ray detector stored in another inspection room is used for the X-ray imaging in a self inspection room, the radiation technician, and the like, have been required to go to the other inspection room in order to check the inspection results on the X-ray detector, and it has not been easy to check the inspection results.

Further, in the techniques disclosed in the patent gazettes, the items related to the operation in the actual operation conditions for the X-ray detector are not inspected during the storage. Therefore, supposing that those items are not inspected during the storage, and a disqualified X-ray detector having defects or abnormalities is used for the X-ray imaging on the subject without checking the inspection results during the storage, there have been problems such that a desired image is not obtained and unnecessary exposure is generated.

The embodiments are intended to solve the above problems and provide a management system of X-ray detectors and an X-ray diagnosis apparatus, capable of checking the inspection results easily and preventing the generation of unnecessary exposure.

BRIEF DESCRIPTION OF THE DRAWINGS

FIG. 6 is a time chart illustrating a series of operation from activating the system until shutting down the system in the management system of the X-ray detectors according to a second embodiment.

DETAILED DESCRIPTION

A management system of the X-ray detectors according to the embodiments detects X-rays irradiated from the X-ray generator when X-ray imaging is carried out, and includes an inspection unit and a validity period setting unit. The inspection unit inspects at least one of performance, function, and operation of an actual operation state of the X-ray detector. The validity period setting unit sets a validity period which is a criterion for determining whether the inspection results inspected are valid or not. The system is configured such that X-ray imaging is not performed on a subject when the inspection results are determined to be invalid based on the validity period.

Figure 1:
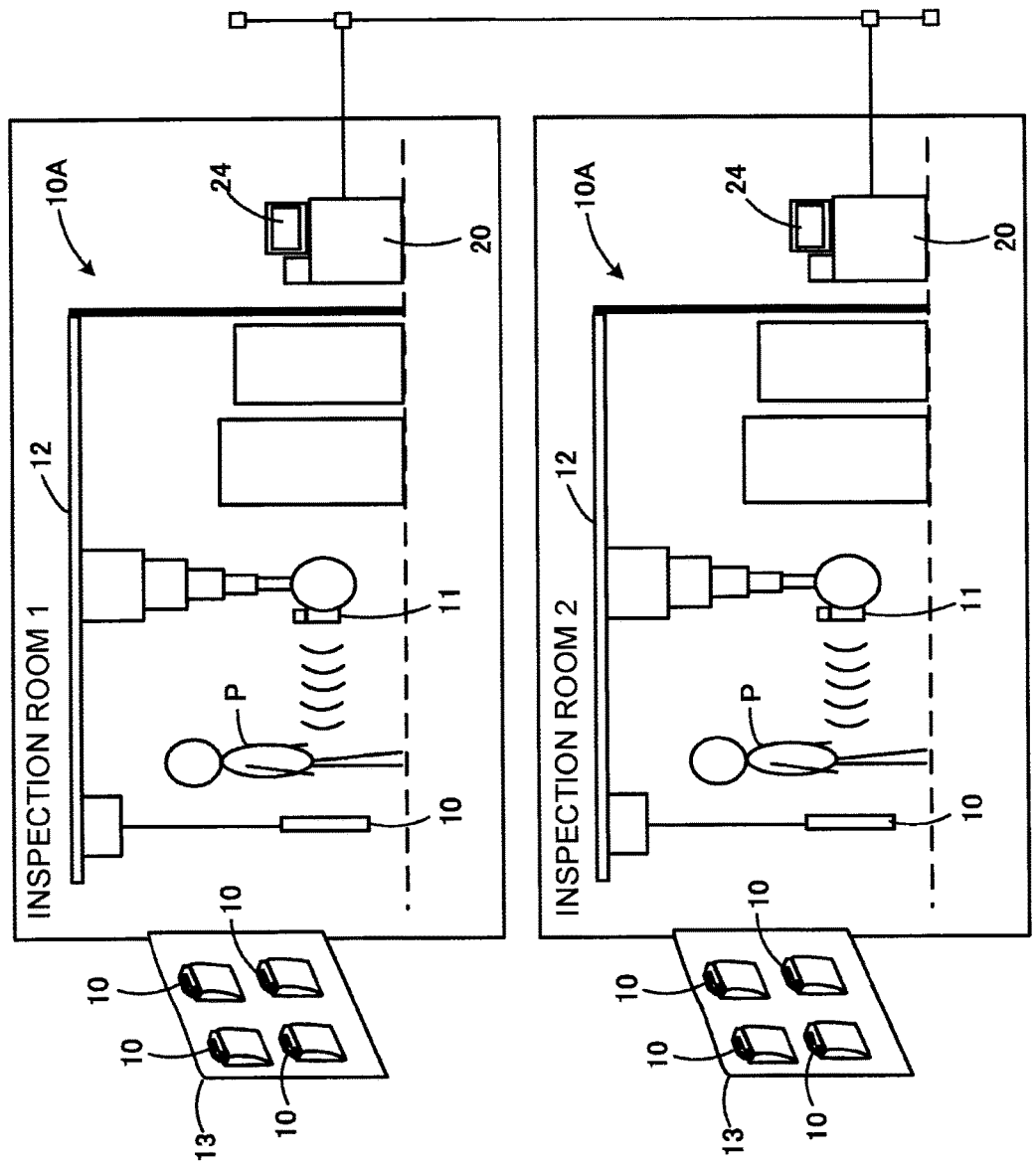
FIG. 1 is a conceptual diagram of inspection rooms and X-ray diagnosis apparatuses.

With reference to FIG. 1, the inspection rooms and the X-ray diagnosis apparatuses are described. FIG. 1 is a conceptual diagram of the inspection rooms and X-ray diagnosis apparatuses 10A. FIG. 1 illustrates an inspection room 1 and an inspection room 2. Here, each of the inspection rooms and the X-ray diagnosis apparatuses 10A provided respectively thereto have the same configuration. Hereinafter, the inspection room 1 and the X-ray diagnosis apparatus 10A provided thereto are described as representatives, and the description of the inspection room 2 and the X-ray diagnosis apparatus 10A provided thereto is omitted.

As shown in FIG. 1, the X-ray diagnosis apparatus 10A includes X-ray detectors 10, an X-ray generator 11, a transferring mechanism 12, and a console 20. The X-ray detector 10 and the X-ray generator 11 are height adjustable and transferable along a ceiling with the transferring mechanism 12. The X-ray detector 10 detects X-rays which are generated from the X-ray generator 11 and transmitted through a subject (patient) P. Based on the detected results, an image is produced and displayed on a display 24.

A dock 13 is arranged in the inspection room 1 in FIG. 1. A plurality (4, for example) of the X-ray detectors 10 is housed in the dock 13. Each of the X-ray detectors 10 has a self diagnosis unit 50 (described later). In routine inspection in which. inspection is indirectly/regularly performed on the self diagnosis results diagnosed by the self diagnosis unit 50, the first items are inspected. At the time of the operation-start inspection that is when the X-ray detector 10 is arranged at the position facing the X-ray generator 11, the second items are inspected. These inspection results are stored, in a data storage 40 (described later) provided inside the console 20, which can be read by other devices (here, the other console 20 in the inspection room 2). The console 20 is connected to the other console 20 in the inspection room 2 via local area network (LAN). Thereby, the inspection results stored in the data storage 40 provided inside the console 20 in one of the inspection room is read by the console 20 in the other inspection room. These inspection results are used when a controller of the X-ray diagnosis apparatus permits the start of a diagnostic photographing mode. Further, these inspection results can be checked by the radiation technician, and the like, by being displayed on the display 24 in both of the self inspection room and the other inspection room.

That is, it is possible to easily check the inspection results on the X-ray detector 10 from multiple places within the medical institution, and prevent the generation of unnecessary exposure since a suitable X-ray detector 10 is used for the X-ray imaging for diagnosis to obtain an image desired.

[First Embodiment]

A first embodiment of the management system of the X-ray detectors 10 is described with reference to respective drawings.

Figure 2:
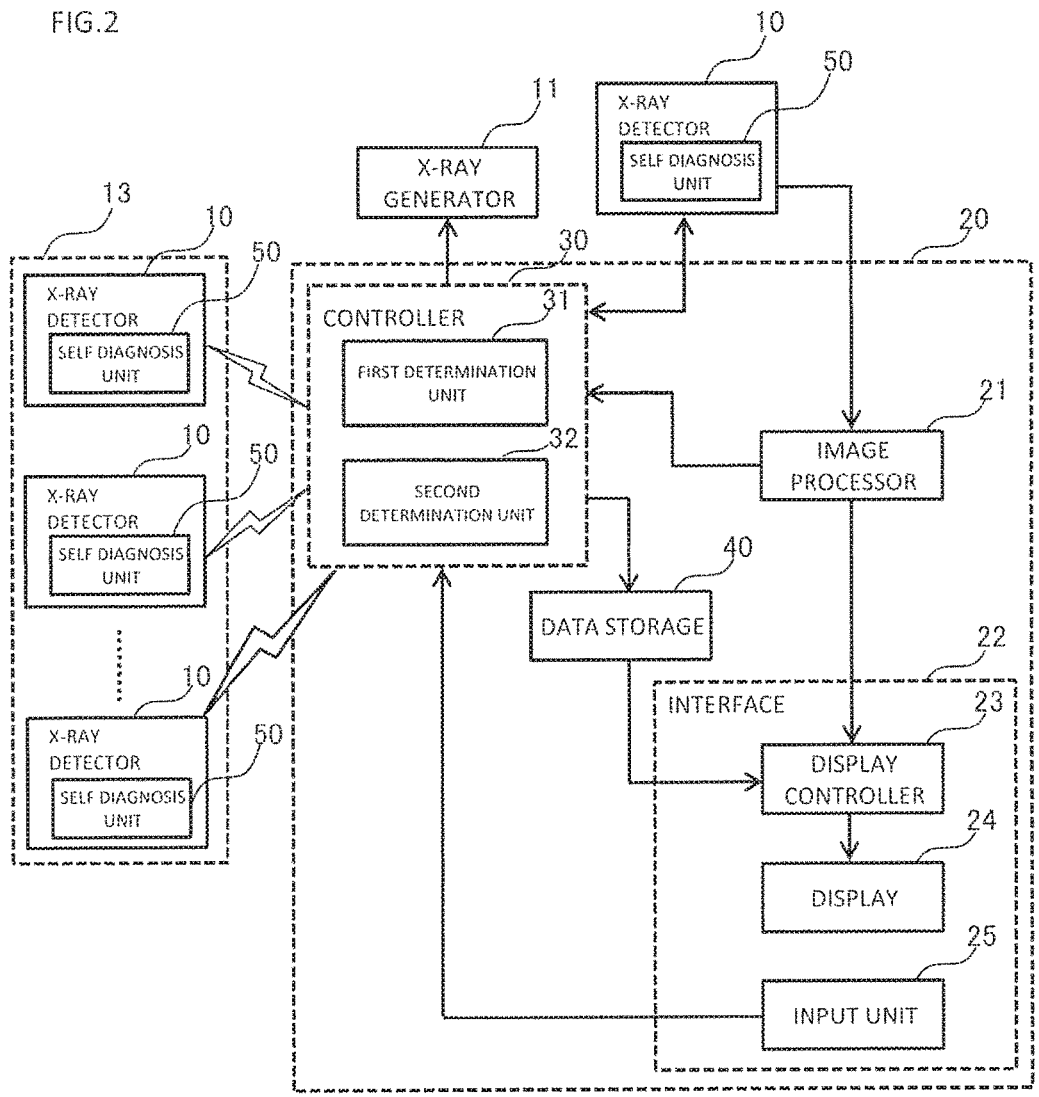
FIG. 2 is a configuration block diagram of a management system of X-ray detectors according to a first embodiment.

Firstly, the basic configuration of the management system of the X-ray detectors 10 is described with reference to FIG. 2. FIG. 2 is a configuration block diagram of the management system of the X-ray detectors 10.

As shown in FIG. 2, the management system of the X-ray detectors 10 includes an image processor 21, an interface 22, a controller 30, and the data storage 40. The controller 30 is an example of an "inspection unit".

The image processor 21 produces an image by performing the filter processing and the gradation processing based on the X-rays detected by the X-ray detector 10 in the X-ray imaging. The interface the controller 30, and the data storage 40 are arranged in the console 20. The interface 22 includes a display controller 23, the display 24, and an input unit 25. The display controller 23 causes the display 24 to display the image produced by the image processor 21. The controller 30 has the diagnostic photographing mode for performing the X-ray imaging on the subject P, and inspection modes for performing inspection on the X-ray detectors 10. The controller 30 performs basic image quality inspection (described later) of the X-ray image on reception of the image generated by the image processor 21 at the inspection mode.

(Routine Inspection)

Next, a routine inspection, as an example of the inspection mode, is described. The timing of the routine inspection may not be only when the X-ray detectors 10 are housed in the dock 13 but also when the start-operation inspection (described later) is performed.

In FIG. 2, the X-ray detectors 10 housed in the dock 13 are conceptually illustrated. As shown in FIG. 2, each of the X-ray detectors 10 has the self diagnosis unit 50 for diagnosing the operation states of detecting elements configuring the detector. The self diagnosis unit 50 diagnoses the operation states of the detecting elements configuring the X-ray detector 10 intermittently/regularly (for example, at hourly intervals) when the X-ray detectors 10 are housed in the dock 13. The controller 30 inspects the self diagnosis results diagnosed by the self diagnosis unit 50. This inspection is called "first item inspection". Here, the "first item inspection" includes inspection, including A) dark image inspection, B) defective pixel inspection, C) battery condition inspection, and D) wireless communication system inspection.

Here, the "dark image inspection" inspects whether image data produced with the image collected without irradiating X-rays, a dark current of each part of the X-ray detectors 10, and an offset voltage is matched with reference data. Further, the "defective pixel inspection" inspects whether the position of the pixel having the output remarkably different from the peripheral pixels among the output of each pixel in the dark image is within an allowable range. Furthermore, the "wireless communication system inspection" inspects whether the communication can be performed properly with the reference signal intensity.

As shown in FIG. 2, the self diagnosis unit 50 is connected to the controller 30 of the console 20 via the wireless LAN. With the wireless communication system, the self diagnosis results on the first items in the routine inspection are regularly transmitted from the self diagnosis unit 50 to the controller 30. The controller 30 inspects the self diagnosis results, and causes the data storage 40 to update and store the inspection results which can be read by the other devices.

The inspection results on the first items and the identification number (detector ID) of the X-ray detector are recorded inside the system (the data storage 40 in the system). The data storage 40 may be provided inside the X-ray detector 10 (described later).

As described above, in the routine inspection, the inspection results on the first items are automatically stored in the data storage 40, and any manual operations by the radiation technician, and the like, are not required.

(Start-operation Inspection)

Next, a start-operation inspection, which is an example of an inspection mode, is described. In the start-operation inspection, the routine inspection described earlier may also be performed.

The X-ray detector 10 to be subjected to the start-operation inspection is selected from the plurality of X-ray detectors 10 subjected to the routine inspection.

For the selected X-ray detector 10, the display controller 23 can cause the display 24 to display the inspection results on the first items stored in the data storage 40, on reception of the operation of the input unit 25 by the radiation technician, and the like. Thereby, the inspection results on the first items are checked by the radiation technician, and the like. The checking of the inspection results on the first items may be performed not manually but by the controller. Based on the inspection results, the start-operation inspection is performed when the selected X-ray detector 10 is normal. On the other hand, when the selected X-ray detector 10 is abnormal, for example, the start-operation inspection is not performed, the X-ray detector 10 is not returned to the dock 13, but the cause of the abnormality is determined.

Desirable information at the time of starting the start-operation inspection is the inspection results on the first items coincident with the identification number of the X-ray detector selected; however, it does not mean that the information is necessary. This is because the inspection results on the first items are the information which can be obtained by performing the inspection after the start-operation inspection is started.

The controller 30 performs the actual operation inspection on each of the X-ray detectors 10 under the actual operation conditions at the time of the X-ray imaging, on reception of the inspection instruction, when the X-ray detector 10 is arranged at the position facing the X-ray generator 11. This inspection is called "second item inspection". Here, the "second item inspection" includes inspection, including E) inspection of the timing with the X-ray irradiation of the X-ray generator 11, F) inspection under the actual use state of the wireless communication system, and G) basic image quality inspection of an X-ray image.

Here, the "basic image quality inspection of an X-ray image" includes imaging a flat field image and a predetermined phantom image, and performing inspection whether the basic image quality, such as image level uniformity, space resolution, contrast resolution, image distortion, and the like, is matched with the reference data. As described above, on reception of the instruction by the operation of the input unit 25, the controller 30 may perform the routine inspection in the start-operation inspection. At this time, the inspection on the first items is performed when the X-ray detector 10 is arranged at the position facing the X-ray generator 11 and the start-operation inspection is started. After the routine inspection is carried out, the inspection results on the first items are stored in the data storage 40 to be read by the other devices if the inspection results are normal. Subsequently, the inspection on the second items is carried out, and the results on the second items are stored in the data storage 40 to be read by the other devices.

The controller 30 causes the data storage 40 to store the inspection results on the second items in the start-operation inspection to be read by the other devices. The inspection results on the second items are stored inside the system (the data storage 40 in the system). The data storage 40 may be provided inside the X-ray detector 10 (described later).

On reception of the operation of the input unit 25 by the radiation technician, and the like, the display controller 23 can cause the display 24 to display the inspection results on the second items stored in the data storage 40. Thus, the inspection results on the second items are checked by the radiation technician, and the like. When it is determined that inspection results for the X-ray detector 10 are normal, the X-ray detector 10 is returned to the dock 13 or the X-ray imaging for diagnosis is performed. On the other hand, when it is determined that the X-ray detector 10 is abnormal, the X-ray detector 10 is not returned to the dock 13, and the cause of the abnormality is determined.

At the time of the starting of the X-ray imaging for diagnosis, the inspection results on the second items are determined as follows.

(First Determination Unit 31)

The controller 30 includes a first determination unit 31. The first determination unit 31 is another example of the "inspection unit". The first determination unit 31 determines whether the inspection results on the second items at the operation-start inspection are normal or not. Here, "the inspection results are normal" means that the inspection results are matched with criterions. The "criterions" are, for example, A) reference data at the dark image inspection, D) reference signal intensity at the wireless communication system inspection, and G) reference data at the basic image quality inspection of an X-ray image.

On reception of the determination results that the inspection results are not normal by the first determination unit 31, the controller 30 controls the interface 22 of the console 20, the X-ray detector 10, and the X-ray generator 11 so that the X-ray imaging can not be performed on the subject P regardless of the instruction of the X-ray imaging for diagnosis. Further, the display controller 23 causes the display 24 to display the determination results by the first determination unit 31. The determination results are included in the inspection results. The display controller 23 causes the display 24 to display the inspection results by the controller 30 and the determination results by the first determination unit 31.

(Operation)

Hereinabove, the configuration of the management system of the X-ray detectors has been briefly described.

Figure 4:
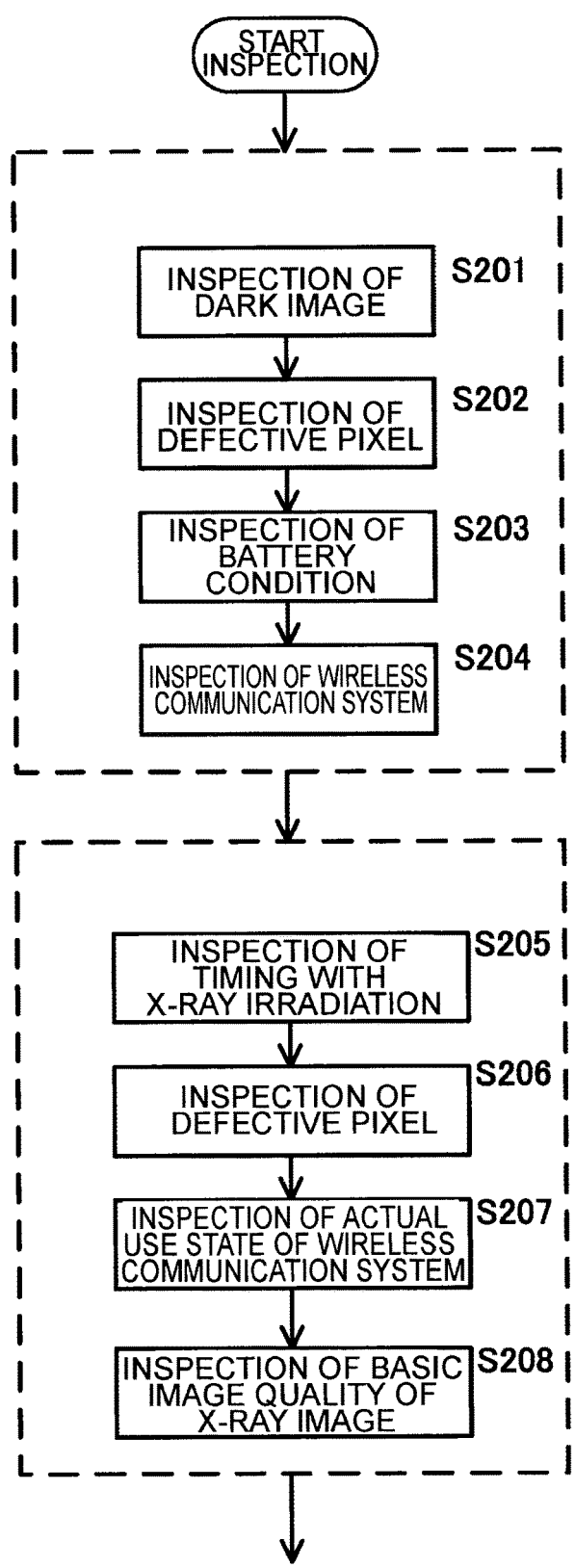
FIG. 4 is a flowchart illustrating a series of operation for inspection.
Figure 5:
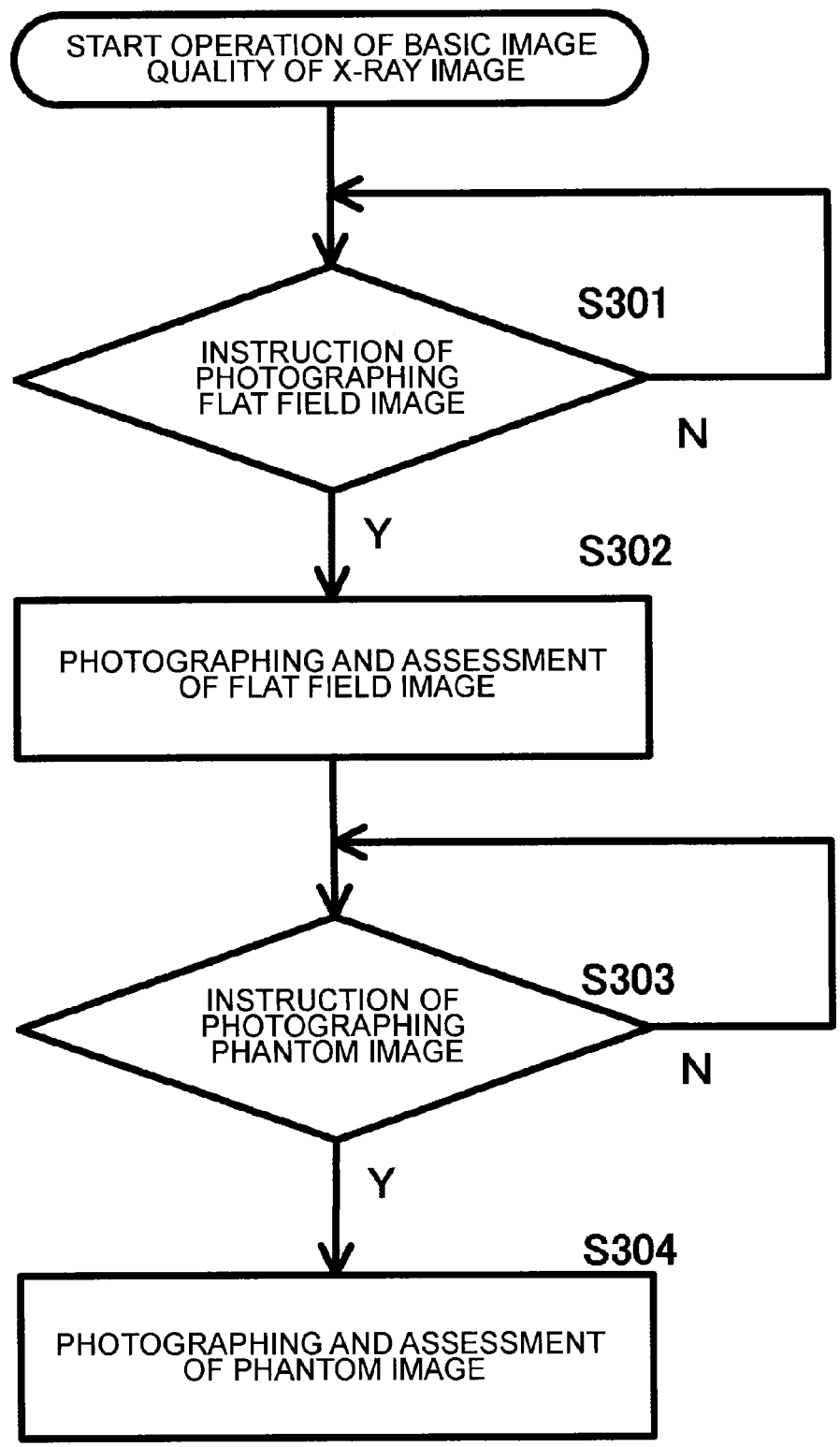
FIG. 5 is a flowchart illustrating a series of operation for basic image quality inspection for an X-ray image.

Next, a series of operation of the management system of the X-ray detectors is described with reference to FIG. 3, FIG. 4, and FIG. 5.

Figure 3:
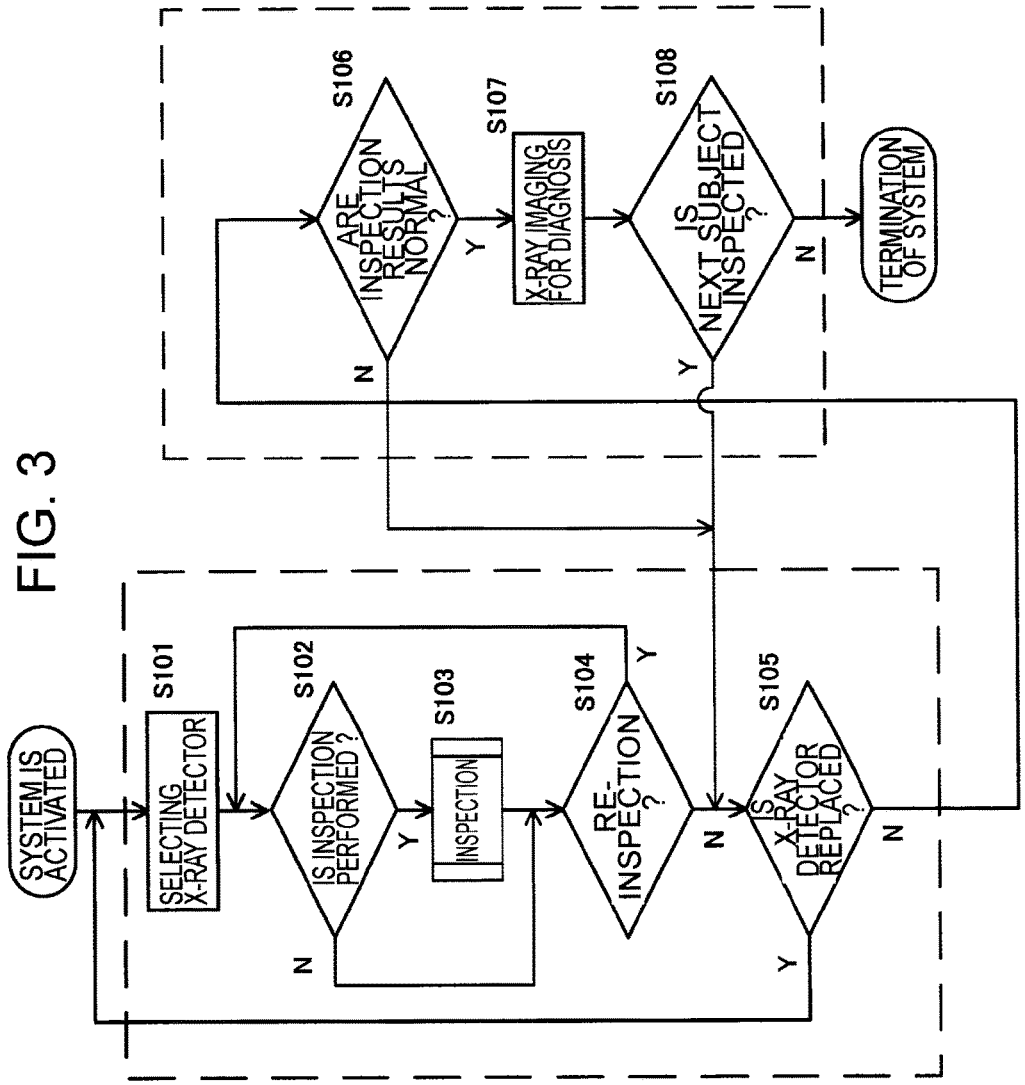
FIG. 3 is a flowchart illustrating a series of operation from selecting the X-ray detector until performing X-ray imaging.

FIG. 3 is a flowchart illustrating the series of operation from selecting the X-ray detector until performing the X-ray imaging for diagnosis. Here, it is described a situation that when the X-ray detector 10 is arranged at the position facing the X-ray generator 11, the routine inspection and the start-operation inspection are performed (the routine inspection is performed in the start-operation inspection).

Firstly, the X-ray detector 10 is selected (step S101). The selection of the X-ray detector 10 is performed when the X-ray detector 10 is arranged at the position facing the X-ray generator 11. The identification number of the selected X-ray detector 10 is stored in the data storage 40.

Next, on reception of the instruction by the operation of the input unit 25, the controller 30 determines whether the inspection is performed or not (step S102). When the controller 30 determines that the inspection is performed (step S102: Y), the controller 30 inspects the X-ray detector 10 selected (step S103).

Here, the inspection detail is described with reference to FIG. 4. FIG. 4 is a flowchart illustrating the series of operation of the inspection.

Firstly, the routine inspection is performed (steps S201 to S204). Next, the start-operation inspection is then performed (steps S205 to S208).

As an example of the implementation order in the routine inspection, firstly the controller 30 inspects the diagnosis results of the dark image by the self diagnosis unit 50 (step S201). The controller 30 then inspects the diagnosis results of the defective pixel by the self diagnosis unit 50 (step S202). Next, the controller 30 inspects the diagnosis results of the battery conditions by the self diagnosis unit 50 (step S203). Subsequently, the controller 30 inspects the diagnosis results of the wireless communication system by the self diagnosis unit 50 (step S204).

As an example of the implementation order in the start-operation inspection, firstly the controller 30 inspects the timing with the X-ray irradiation (step S205). The controller 30 then inspects the defective pixel (step S206). Next, the controller 30 inspects the actual use state of the wireless communication system (step S207). Subsequently, the controller 30 inspects the basic image quality of the X-ray image (step S208).

Here, the basic image quality of the X-ray image is described in detail with reference to FIG. 5. FIG. 5 is a flowchart illustrating the series of operation of the basic image quality of an X-ray image.

Firstly, the controller 30 determines whether an instruction of the flat field image photographing is received or not (step S301). When the controller 30 determines that the instruction of the flat field image photographing is received (step S301: Y), photographing of the flat field image is performed, and the controller 30 assesses the flat field image (step S302).

The controller 30 then determines whether an instruction of the phantom image photographing is received or not (step S303). When the controller 30 determines that the instruction of the phantom image photographing is received (step S303: Y), photographing of the phantom image is performed, and the controller 30 assesses the phantom image (step S304).

The inspection is terminated through the dark image inspection (step S201) to the basic image quality inspection of the X-ray image (step S208) described above.

The controller 30 than determines whether re-inspection is performed or not (step S104). When the controller 30 determines that the instruction is not performed (step S102: N), it proceeds to step S104.

When the controller 30 determines that the re-inspection is performed (step S104: Y), it proceeds back to step S102. When the controller 30 determines that the re-inspection is not performed (step S104: N), the controller 30 determines whether the X-ray detector 10 is replaced or not in response to either the instruction by the operation of the input unit 25 or a fact that the X-ray detector 10 is released from the position facing the X-ray generator 11 (step S105).

When the controller 30 determines that the X-ray detector 10 is replaced (step S105: Y), it proceeds back to step S101 at which the X-ray detector 10 is selected.

When the controller 30 determines that the X-ray detector 10 is not replaced (step S105: N), the first determination unit 31 determines whether the inspection results are normal or not (step S106). On reception of the determination results by the first determination unit 31, the display controller 23 causes the display 24 to display the inspection results (including the determination results).

When the first determination unit 31 determines that the inspection results are normal (step S106: Y), the controller 30 controls the X-ray detector 10 and the X-ray generator 11 to cause the X-ray imaging for diagnosis to be performed (step S107).

When the first determination unit 31 determines that the inspection results are abnormal (step S106: N), it proceeds back to step S105 at which it is determined that whether the X-ray detector 10 is replaced or not. When the first determination unit 31 determines that the inspection results on the replaced X-ray detector 10 are normal (step S106: Y), the controller 30 causes the X-ray imaging for diagnosis to be performed; however, the controller 30 does not cause the X-ray imaging for diagnosis to be performed unless the first determination unit 31 determines that the inspection results are normal.

After the X-ray imaging for diagnosis is completed, on reception of the instruction by the operation of the input unit 25, the controller 30 determines that whether the next subject P is inspected or not (step S108). When it is determined that the next subject P is inspected (step S108: Y), it proceeds back to step S105 at which it is determined that the X-ray detector 10 is replaced or not. When it is determined that the next subject P is not inspected (step S108: N), the process is terminated.

[Second Embodiment]

Next, a second embodiment of the management system of the X-ray detectors 10 is described with reference to figures. In the second embodiment, configurations that are the same as those in the first embodiment are denoted with the same numerals, and explanations thereof are omitted, and configurations that are different from those in the first embodiment are mainly described.

The controller 30 includes a timer (not shown), and a second determination unit 32 (see FIG. 2). The second determination unit 32 is another example of the "inspection unit". The timer measures an elapsed time from the start of recording the inspection results on the second items in the start-operation inspection. The second determination unit 32 determines that whether the elapsed time measured by the timer exceeds the determined validity period or not. The validity period is stored in the data storage 40. At the time of starting the X-ray imaging for diagnosis, the information whether the elapsed time exceeds the validity period or not is required. The console 20 including the interface 22, the controller 30, and the data storage 40 is an example of a "validity period setting unit", The controller 30 controls the X-ray detector 10 and the X-ray generator 11 not to perform the X-ray imaging for diagnosis, on reception of the determination results by the second determination unit 32 when the elapsed time exceeds the validity period. The recording location of the information whether the elapsed time exceeds to the validity time is the inside of the system (the data storage 40 in the system).

FIG. 6 is a time chart illustrating a series of operation from activating the system to shutting down the system. Here, the validity period is set as "24 hours" and described.

As shown in FIG. 6, on the first day, the system is activated on reception of the instruction by the operation of the input unit 25. The first determination unit 31 then determines that the inspection results on the second items in the start-operation inspection are normal, and when the second determination unit 32 determines that the elapsed time does not exceed the validity period, the X-ray imaging for diagnosis can be performed.

In the first embodiment, in step S106 in FIG. 3, the first determination unit 31 determines that the inspection results on the second items in the start-operation inspection are normal; however, in the second embodiment, the start-operation inspection is reliably implemented at a certain cycle since the validity of the inspection results is additionally determined. Thus, the X-ray imaging for diagnosis using an unqualified X-ray detector 10 is prevented, and unnecessary exposure can be reduced. For example, on reception of the instruction by the operation of the input unit 25, if the validity period is adjustably configured, the start-operation inspection can then be implemented at an inspection cycle matching with the inspection terms of the medical institution.

Further, the display controller 23 causes the display 24 to display the inspection results by the controller 30 and the determination results by the second determination unit 32, as the inspection results. Thus, the inspection results are easily checked by the radiation technician, and the like.

The elapsed time after obtaining the inspection results in the start-operation inspection on the first day is illustrated with solid lines in FIG. 6. As shown in FIG. 6, after the system is activated on the second day, when the validity period (24 hours) exceeds after obtaining the inspection results in the start-operation inspection on the first day, the controller 30 controls the X-ray detector 10 and the X-ray generator 11 not to perform the X-ray imaging for diagnosis. At this time, the display controller 32 causes the display 24 to display a fact that the elapsed time exceeds the validity period (24 hours). By displaying the fact, the radiation technician, and the like, are urged to implement the start-operation inspection.

The elapsed time after obtaining the inspection results in the start-operation inspection on the second day is illustrated with broken lines in FIG. 6. When the inspection results in the start-operation inspection on the second day is obtained, the validity period (24 hours) elapses after the system is activated on the third day.

[Third Embodiment]

Figure 7:
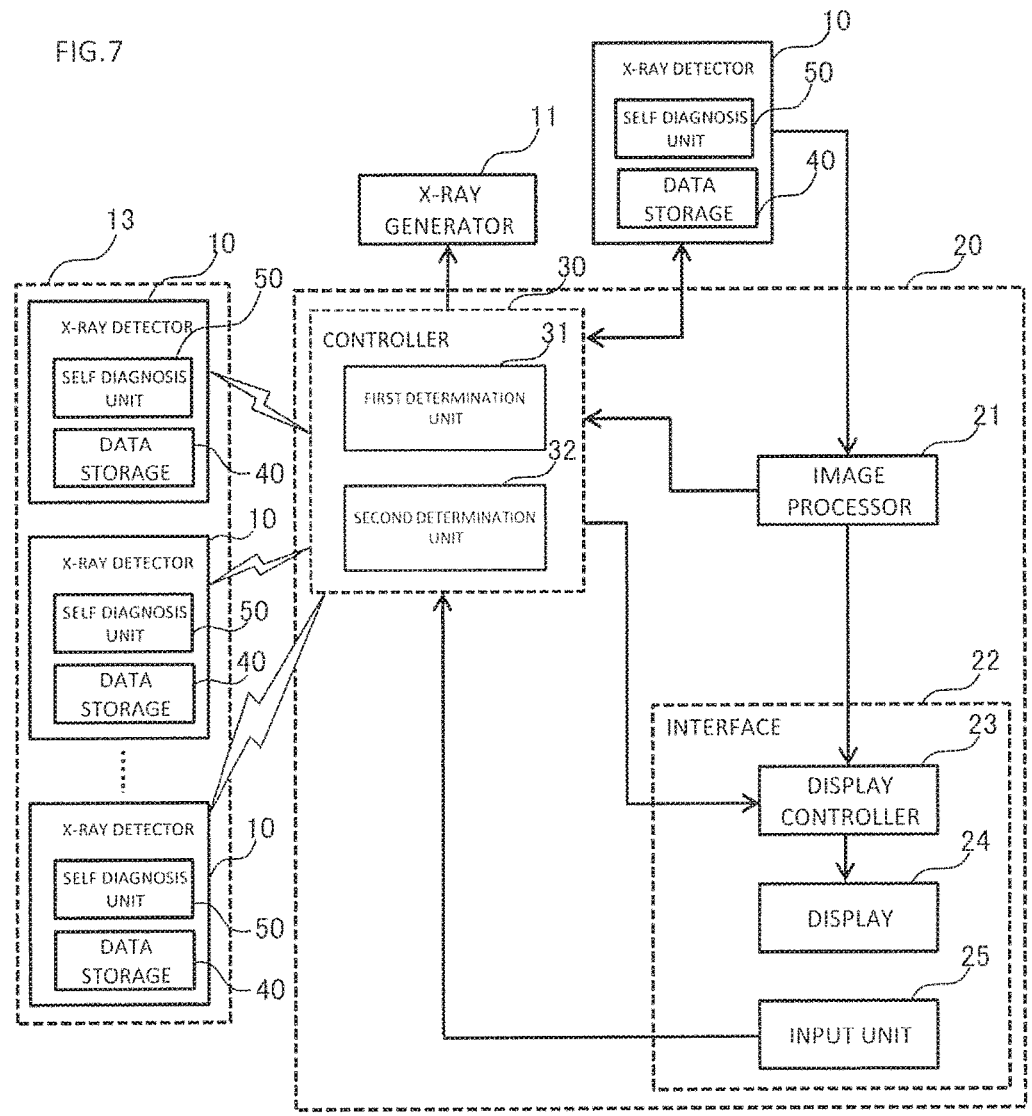
FIG. 7 is a configuration block diagram of the management system of the X-ray detectors according to a third embodiment.

Next, a third embodiment of the management system of the X-ray detectors 10 is described with reference to FIG. 7. FIG. 7 is a configuration block diagram of the management system of the X-ray detectors 10 according to the third embodiment. In the third embodiment, configurations that are the same as those in the first embodiment are denoted with the same numerals, and explanations thereof are omitted, and configurations that are different from those in the first embodiment are mainly described.

It is shown that the data storage 40 is provided inside the console 20 (in the system) in the first embodiment; however, the data storage 40 is provided inside the X-ray detector 10 in the third embodiment, as shown in FIG. 7.

The recording location for the inspection results on the first items in the routine inspection, the inspection results on the second items in the start-operation inspection, and the information whether the elapsed time exceeds the validity period or not is inside of the system (the data storage 40 in the system). The data storage 40 may be provided to the X-ray detector 10 itself.

[Fourth Embodiment]

Next, a fourth embodiment of the management system of the X-ray detectors 10 is described. In the first embodiment, the inspection results by the controller 30 and the determination results by the first determination unit 31 are displayed on the display 24 of the interface 22. Further, in the second embodiment, the inspection results by the controller 30 and the determination results by the second determination unit 32 are displayed on the display 24 of the interface 22.

On the contrary, in the forth embodiment, a display may be provided to the X-ray detector 10. The display of the X-ray detector 10 typically has a small display region with respect to the display 24 of the interface 22. For limited information, it is displayable in the small display region. Thus, it is configured such that the determination results by the first determination unit 31 and the determination results by the second determination unit 32, as the inspection results, are displayed on the display of the X-ray detector 10.

In the embodiments described above, the controller 30 (the first determination unit 31 and the second determination unit 32) and the data storage 40 are provided as the configuration parts of the management system of the X-ray detectors 10; however, the controller 30, and the like, may be the configuration parts of the X-ray diagnosis apparatus.

Also, in the embodiments described above, each of the X-ray detectors has the self diagnosis unit for diagnosing the operation states of the detecting elements configuring the detector; however, the diagnosis unit may be included in the management system or the X-ray diagnosis apparatus, and the operation states may be diagnosed by operating the detecting elements in accordance with the instruction of the management system or the X-ray diagnosis apparatus.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of embodiments described herein may be made without departing from the spirit of the inventions. The accompanying claims and their equivalents are intended to cover such forms or modifications as would fall within the scope and spirit of the inventions.

What is claimed is:

1. A management system of X-ray detectors which detect X-rays irradiated from an X-ray generator to perform X-ray imaging, the management system comprising:
   processing circuitry configured to
      inspect at least one item related to at least one of performance, function, and operation of an operation state of an X-ray detector of the X-ray detectors,
      set a validity period to establish whether inspection results inspected are valid or not,
      control the X-ray generator during the X-ray imaging,
      determine whether the inspection results at operation-start inspection are normal or not, and
      determine whether elapsed time from start of recording the inspection results exceeds the validity period or not,
   wherein even when the inspection results are normal, when the elapsed time exceeds the validity period and the inspection results are determined to be invalid based on the validity period, the processing circuitry controls the X-ray detectors and the X-ray generator such that the X-ray imaging is not performed on a subject.

2. The management system of the X-ray detectors according to claim 1, further comprising a controller configured to control the X-ray detector and the X-ray generator to not perform the X-ray imaging on the subject.

3. The management system of the X-ray detectors according to claim 1, wherein the processing circuitry is configured to inspect at least one of the at least one item related to at least one of the performance, function, and operation of the operation state by irradiating X-rays to the X-ray detector.

4. The management system of the X-ray detectors according to claim 1, wherein the at least one item includes determining presence and/or absence of defects and sensitivity states of detecting elements of the X-ray detector.

5. The management system of the X-ray detectors according to claim 1, further comprising a data storage configured to store the inspection results which can be read by other devices.

6. The management system of the X-ray detectors according to claim 1, further comprising a display that is caused to display the inspection results.

7. The management system of the X-ray detectors according to claim 1, further comprising a display that is caused to display that the inspection results are invalid to prevent the X-ray imaging from being performed on a subject.

8. An X-ray diagnosis apparatus storing a plurality of X-ray detectors, and comprising:
an X-ray generator which irradiates X-rays to any one of the plurality of X-ray detectors; and
processing circuitry which controls the X-ray detector and the X-ray generator to perform X-ray imaging, the processing circuitry being configured to
diagnose operation states of detecting elements configuring an X-ray detector of the X-ray detectors,
for a diagnostic photographing mode, perform X-ray imaging on a subject, and for inspection modes, inspect the X-ray detector,
in the inspection mode, inspect regularly diagnosis results of a diagnosis performed by the processing circuitry, and perform operation inspection on each of the X-ray detectors in an operation state of the X-ray imaging, and
set a validity period to establish whether inspection results inspected are valid or not,
wherein the processing circuitry is further configured to
determine whether the inspection results at operation-start inspection are normal or not,
determine whether elapsed time from start of recording the inspection results exceeds the validity period or not, and
even when the inspection results are normal, control the X-ray detector and the X-ray generator not to perform the X-ray imaging on a subject when the elapsed time exceeds the validity period and the inspection results are determined to be invalid based on the validity period.

9. The management system of the X-ray detectors according to claim 2, wherein the processing circuitry is configured to inspect at least one of the at least one item related to at least one of the performance, function, and operation of the operation state by irradiating X-rays to the X-ray detector.

* * * * *